(12) United States Patent
Sutherland

(10) Patent No.: US 10,603,450 B2
(45) Date of Patent: Mar. 31, 2020

(54) COMPLIANCE MONITOR FOR A DRY POWDER MEDICAMENT DELIVERY DEVICE

(71) Applicant: ADHERIUM (NZ) LIMITED, Auckland (NZ)

(72) Inventor: Garth Campbell Sutherland, Auckland (NZ)

(73) Assignee: ADHERIUM (NZ) LIMITED, Auckland (NZ)

(*) Notice: Subject to any disclaimer, the term of this patent is extended or adjusted under 35 U.S.C. 154(b) by 498 days.

(21) Appl. No.: 15/119,361

(22) PCT Filed: Sep. 4, 2014

(86) PCT No.: PCT/NZ2014/000189
§ 371 (c)(1),
(2) Date: Aug. 16, 2016

(87) PCT Pub. No.: WO2015/133909
PCT Pub. Date: Sep. 11, 2015

(65) Prior Publication Data
US 2017/0246406 A1 Aug. 31, 2017

(30) Foreign Application Priority Data
Mar. 3, 2014 (NZ) ........................................ 622000

(51) Int. Cl.
*A61M 15/00* (2006.01)
(52) U.S. Cl.
CPC ...... *A61M 15/0065* (2013.01); *A61M 15/008* (2014.02); *A61M 15/0025* (2014.02);
(Continued)

(58) Field of Classification Search
CPC ............ A61J 7/0418; A61K 2039/505; A61K 47/6825; A61K 47/6849; A61K 47/6851;
(Continued)

(56) References Cited

U.S. PATENT DOCUMENTS 5,331,953 A * 7/1994 Andersson ............ A61M 15/00
128/200.14
5,505,195 A * 4/1996 Wolf .................. A61M 15/0045
128/200.23
(Continued)

FOREIGN PATENT DOCUMENTS

NZ 614928 6/2014
WO 00/64517 A1 11/2000
(Continued)

OTHER PUBLICATIONS

International Search Report for PCT/NZ2014/000189 dated Feb. 26, 2015.

*Primary Examiner* — Annette Dixon
(74) *Attorney, Agent, or Firm* — Kenealy Vaidya LLP

(57) ABSTRACT

Some embodiments are directed to a compliance monitor for monitoring patient usage of a dry powder medicament delivery device. The medicament delivery device includes a store of medicament housed within a main body portion, and a base portion which is rotatable with respect to the main body portion. The medicament delivery device also includes a medicament dispenser for dispensing a dose of medicament into an inhalation chamber, a mouthpiece through which the dose of medicament may be inhaled by a user, and a replaceable cap. The compliance monitor includes a first portion for receiving and/or retaining the base portion of the medicament delivery device, and a second portion for releasably securing the medicament delivery device to the first portion.

21 Claims, 6 Drawing Sheets

Figure 1:
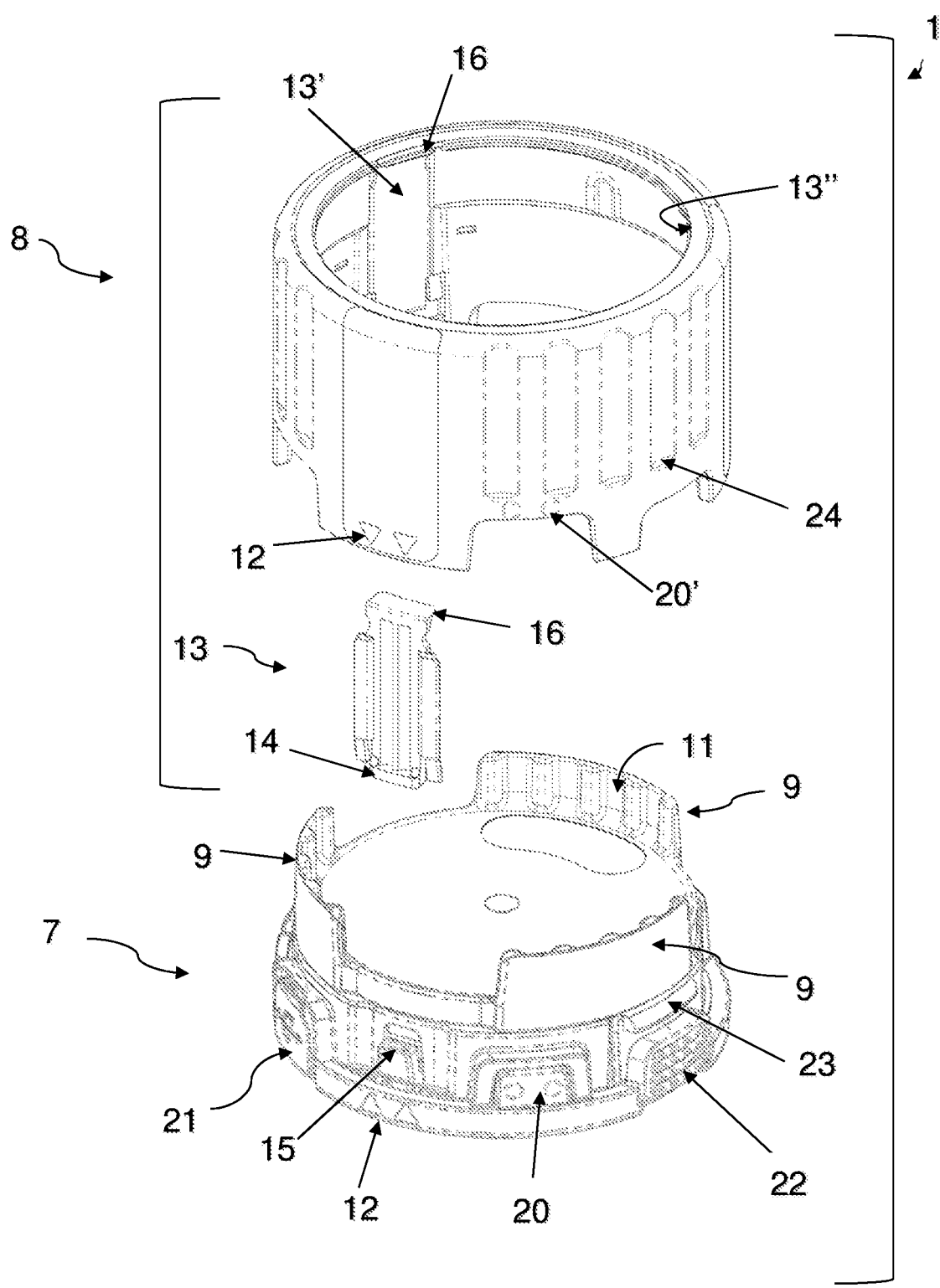

(52) U.S. Cl.
CPC ... *A61M 15/0086* (2013.01); *A61M 2202/064* (2013.01); *A61M 2205/14* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/8206* (2013.01); *A61M 2205/8237* (2013.01); *A61M 2205/8293* (2013.01)

(58) Field of Classification Search
CPC .............. A61K 47/6897; A61M 15/00; A61M 15/0028; A61M 15/0045; A61M 15/0048; A61M 15/0065; A61M 15/0068; A61M 15/0078; A61M 15/008; A61M 15/009; A61M 2016/0021; A61M 2202/064; A61M 2205/0233; A61M 2205/3375; A61M 2205/43; A61M 2205/52; A61M 2206/14; B29C 2791/006; B29C 71/00; B29L 2031/753; B65B 31/00; B82Y 5/00; C07D 401/12; C07K 16/2866; C07K 16/30; C07K 2317/73; C07K 2317/77; G06K 7/10297; G06M 1/246; H04B 5/0031
USPC ............. 128/200.14, 200.23, 203.14, 203.15
See application file for complete search history.

(56) References Cited

U.S. PATENT DOCUMENTS

| | | | |
|---|---|---|---|
| 6,076,521 A * | 6/2000 | Lindahl ............ | A61M 15/0065 128/200.23 |
| 8,424,517 B2 | 4/2013 | Sutherland et al. | |
| 8,567,394 B2 | 10/2013 | Herder et al. | |
| 2004/0187869 A1 | 9/2004 | Bjorndal et al. | |
| 2007/0107721 A1* | 5/2007 | Olsson ................. | A61M 15/00 128/200.23 |
| 2010/0192946 A1 | 8/2010 | Oi et al. | |
| 2010/0192948 A1 | 8/2010 | Sutherland et al. | |
| 2011/0226242 A1 | 9/2011 | Von Hollen et al. | |
| 2014/0000598 A1 | 1/2014 | Sutherland et al. | |
| 2016/0228657 A1 | 8/2016 | Sutherland | |

FOREIGN PATENT DOCUMENTS

| | | |
|---|---|---|
| WO | 03/092773 A1 | 11/2003 |
| WO | 2008/079350 A2 | 7/2008 |
| WO | 2010/023591 A2 | 3/2010 |
| WO | 2011/083377 A1 | 7/2011 |
| WO | 2011/130583 A2 | 10/2011 |
| WO | 2013/043063 A1 | 3/2013 |

* cited by examiner

COMPLIANCE MONITOR FOR A DRY POWDER MEDICAMENT DELIVERY DEVICE

CROSS REFERENCE TO RELATED APPLICATION

This application is a National Phase filing under 35 C.F.R. § 371 of and claims priority to International Application No.: PCT/NZ2014/000189, filed on Sep. 4, 2014, which claims the priority benefit under 35 U.S.C. § 119 of New Zealand Application No.: 622000, filed on Mar. 3, 2014, the contents of which are hereby incorporated in their entireties by reference.

FIELD

This invention relates to a compliance monitor for a dry powder medicament delivery device. The invention may be particularly suitable for use with dry powder inhalers used in the treatment of respiratory diseases such as asthma, COPD, cystic fibrosis, and bronchiectasis.

However, it is to be understood and appreciated that the invention is not to be limited to such use. For example, the compliance monitor could also be used with other dry powder medicament delivery devices, such as those used for the treatment of pain, heart conditions, erectile dysfunction, diabetes, and so on.

The prior art and possible applications of the invention, as discussed below, are therefore given by way of example only.

BACKGROUND

The use of dry powder inhalers for the treatment of respiratory diseases such as asthma, COPD, cystic fibrosis, and bronchiectasis is well known.

There are several different types of dry powder inhalers.

One common type is in the form of a disk, which includes an external lever. The lever may be actuated by a user to deposit a dose of medicament into an inhalation chamber, after which it may be inhaled by the user via a mouthpiece.

Another common type of dry powder inhaler is in the form of a generally tube-shaped body, which includes an internal store of a suitable medicament; a rotatable base for dispensing a single dose of the medicament into an appropriate inhalation chamber; and a mouthpiece, through which a user may inhale the medicament that has been dispensed into the inhalation chamber. Such dry powder inhalers usually come with a removable and replaceable screw-cap, adapted to cover the mouthpiece and tube-shaped body of the inhaler, when the inhaler is not in use.

Usually, a single dose of medicament is dispensed into the inhalation chamber when the rotatable base is rotated as far as it will go in one direction, before being returned to its original starting position. This back-and-forth action only needs to be completed once (for dispensing each dose of medicament) and the user should hear a click when this action has been completed successfully.

An example of such a dry powder inhaler is the TURBUHALER® which is manufactured and marketed by AstraZeneca AB.

Another similar type of rotational dry powder inhaler, which also has a generally tube-shaped body, and which also includes an internal store of a suitable medicament, is known as the TWISTHALER®, and is manufactured and marketed by Merck & Co. The TWISTHALER® is similar to the TURBUHALER®, except that the TWISTHALER® dispenses a dose of medicament when the cap is unscrewed from the tube-shaped body. That is, the unscrewing of the cap from the tube-shaped body portion serves to automatically rotate the tube-shaped body with respect to the base portion, and it is this action which dispenses a dose of medicament into the inhalation chamber.

However, for both types of inhaler, a dose of medicament is dispensed into the inhalation chamber when the base portion is rotated with respect to the tube-shaped body, or vice versa.

Usually, the store of medicament is in the form of a single and solid mass, and the rotating of the base portion with respect to the tube-shaped body (or vice versa) causes internal scrapers to scrape a small amount of medicament from off the single mass, after which the removed medicament is directed into the inhalation chamber—in the form of a metered amount of dry powder.

The dry powder is then inhaled by the user by sucking strongly on the mouthpiece.

The internal workings of both types of inhaler are usually configured to create an enhanced internal airflow when the user is sucking on the mouthpiece—which forces the dry powder medicament out through the mouthpiece, and into the mouth of the user, under significant pressure. These internal workings of the inhaler therefore serve to ensure that a maximum amount of the dry powder medicament reaches, and/or is deposited in, the airways and/or lungs of the user.

A problem or difficulty associated with the use of all medicament inhalers (including dry powder inhalers) is poor medicament compliance. Many studies have shown that users frequently do not take their medicament at the predetermined or prescribed times and/or in the required amounts.

The consequences of this non-compliance are reduced disease control, lower quality of life, lost productivity, hospitalisation and avoidable deaths.

In order to address the issue of poor medicament compliance, there are now available a number of compliance monitoring devices for use with medicament inhalers. However, and to date, the majority of these compliance monitoring devices have been designed for use with pressurised metered dose inhalers, rather than dry powder inhalers (due to the greater popularity or availability of pressurised metered dose inhalers).

However, dry powder inhalers have become ever more popular in recent times, and especially those with a tube-shaped body and rotatable base, such as those described previously. And so it is important to be able to utilise compliance monitoring devices with such dry powder inhalers, just as compliance monitoring devices are used with pressurised metered dose inhalers.

A problem associated with the use of all dry powder inhalers is that users sometimes inadvertently forget to remove the cap from the inhaler prior to inhaling their dose of medicament. Moreover, the user may often not realise that he/she has made this mistake and/or may not realise that he/she did not receive the dose of medicament. This will result in the user not receiving their medicament at the designated time, and this may have dire consequences.

Moreover, some health professionals demonstrate use of a dry powder inhaler with the cap on, and so many new users or patients inadvertently copy this erroneous technique, and are unaware that they have not received a dose of medicament.

The ability to record compliance data generally relating as to when the cap is removed and replaced, and/or how many times the user dispenses (or attempts to dispense) a dose of medicament, with the cap still attached to the mouthpiece, would be very useful and important information, both for training purposes or feedback for the user, as well as for general medicament compliance data gathering purposes.

Furthermore, another problem associated with rotational dry powder inhalers such as TURBUHALER®, is that a user may inadvertently only rotate the rotatable base portion once, in one direction. That is, the user does not rotate the base portion back to its starting point—as is required to dispense a dose of medicament on each use. And this incorrect action may be repeated for the next dose. This results in the user not receiving a dose of medicament each time that they thought they had, which is clearly undesirable.

U.S. Pat. No. 8,567,394 (Herder et al) describes a device which locks a dry powder inhaler and prevents the cap being replaced upon the attainment of certain circumstances (for example, if too many doses have been dispensed or if the medicament supply has been exhausted). However, this arrangement is undesirable and/or somewhat meaningless, as the user can then no longer use the inhaler and/or receive their medicament. This would be of particular concern if the user was about to suffer an exacerbation event.

US Patent Publication No. 2004/0187869 (Bjorndal et al) describes a training device for a dry powder inhaler. It includes a closure cap removably positioned over the mouthpiece, and an actuation assembly in the housing for actuating a start switch upon removal of the closure cap. Whilst Bjornal prevents the inhaler from being used with the cap on, it does not allow for compliance data to be gathered relating to how many times the user attempts to use the inhaler with the cap on—and this information would be useful for providing the user with training feedback and/or allowing a health professional to ascertain if the user has inherent difficulties with operation of the inhaler, which need to be addressed. For example, a patient such as a young child or an elderly person or a person with intellectual disabilities is unlikely to be aware of their mistake and/or be able to learn from it without outside intervention or feedback. Furthermore, another disadvantage associated with Bjornal is that if the user is unable to operate the inhaler (namely when the cap is on), they may become confused and/or disinclined to figure out the problem and/or take their required dose of medicament.

US Patent Publication No. 2011/0226242 (Von Hollen et al) describes an inhaler which is adapted to emit an audible instruction (and/or provide audible usage feedback) upon the cap being removed. However, and as for Bjornal, Von Hollen does not allow for compliance data to be gathered relating to how many times the user attempts to use the inhaler with the cap on and/or when, and how often, the cap is removed and/or closed.

U.S. Pat. No. 6,076,521 (Lindahl et al) describes a dose indicating device adapted for use with breath-actuated dry-powder inhalers such as TURBUHALER.® The device is a separate unit which is mounted on a manoeuvring element of the inhalator (i.e. an additional attachment that fits onto the base of the inhaler (See "A" in FIG. 10 of Lindahl). The device comprises a first element constructed to be mounted on and around an outer wall surface of the manoeuvring element and a second element rotatably mounted on and around the outer surface of the first element for rotation relative to the first element. The first and the second elements are connected by a lug/slot mechanism, which allows for a small range of movement of the first and the second elements relative to each other. The relative movement of the elements is necessary to detect a dose delivery. The dose detection means may be mechanical or electronic. While the Lindahl invention offers some advantage over the prior art in the field of DPI compliance monitors, it also has some disadvantages. For example, the device requires an additional manoeuvring element to be added onto the DPI inhaler. Furthermore, while Lindahl states that the device may be attached to the inhaler releasably, it is unclear as to how such a releasable attachment may work. Moreover, the lug/slot system used to put the device together is not user-friendly, especially in the context of the demographics of the target patient population. That is, children, elderly or infirm patients would struggle to operate the lug system.

Another problem associated with the use of TURBU-HALER® dry powder inhalers, such as those described previously, is that users, having removed the cap, turn the base of the inhaler only one way at the first use and then the other way at the following use. This results in the user taking the measured dose of medicament only at every other use.

Hence, as well as this skewing the compliance data, it results in the user potentially taking half the prescribed dose of the medicament, which is clearly unsatisfactory.

From a compliance monitoring point of view, with respect to the TURBUHALER®, there is no way of differentiating between when a dose of medicament is dispensed during the normal dispensing of a dose of medicament, as compared to when a dose of medicament is inadvertently dispensed when the cap is being removed and/or replaced.

It may therefore also be of advantage if there was available a compliance monitor for a dry powder medicament inhaler which was able to differentiate between when a user dispenses a dose of medicament normally, as compared to when a dose of medicament is inadvertently dispensed when the cap is being removed or replaced.

Our NZ Patent No. 614928 includes reference to an embodiment of such a compliance monitor, which may be used with a TURBUHALER®.

The compliance monitor described in NZ 614928 is very effective, however one possible drawback or limitation associated with this device is that it lacks the ability to detect and/or record when the compliance monitor has been attached to, and/or removed from, the inhaler—or vice versa.

Another possible drawback associated with the compliance monitor described in NZ 614928 is that the compliance monitor, and associated cap detection means, comprise two portions, and these two portions are screwed together (just as the cap is screwed to the inhaler, as described previously). There are several disadvantages associated with such an arrangement.

Firstly, having to screw the two portions of the compliance monitor together can be a fiddly and/or time consuming process. Moreover, sometimes the two portions may be screwed together with the respective threads not having been lined up properly, resulting in the two portions of the compliance monitor not being properly secured and/or with the compliance monitor not working correctly, or not at all.

Secondly, the action of screwing or unscrewing the two portions of the compliance monitor with respect to each other can sometimes inadvertently rotate the rotatable base of the inhaler at the same time, to thus release (or "half release") a dose of medicament into the inhalation chamber (just as the action of screwing or unscrewing the cap from the inhaler can do the same—as described previously).

It may be of advantage therefore if there was available a compliance monitor for a dry powder inhaler that can be readily attached to, and/or removed from, the dry powder inhaler without a screw-fit.

The need for a screw-fit is avoided in a compliance monitor for a dry powder inhaler described in U.S. Pat. No. 5,505,195 Wolf et al. Wolf describes a device adapted for mounting on DPIs designed to monitor and record dose release, whether inhalation was proper, and the removal and reattachment of the DPI. The device consists of an electronic housing, which is installed in place of the end cap of the DPI, an activation sheath which slides over the main body of the inhaler and, optionally, a customized sanitary cap. The key disadvantage of Wolf is that in order to connect the device to a DPI the user must take apart and replace parts of the regulated medical device (DPI) and replace them with additional parts. The customization of the original DPI may compromise its functionality and performance. In particular, the fitting of an additional tubular sheath around the device which facilitates the inhalation flow sensing, may affect the performance of the DPI.

It may be of advantage if there was available a user-friendly compliance monitor that was able to be releasably fitted to a DPI without the need for any additional customization of the DPI itself.

Object

It is an object of the present invention to provide a compliance monitor for monitoring patient usage of a dry powder medicament delivery device, which goes some way towards addressing some of the aforementioned problems or difficulties, or which at the very least provides the public with a useful choice.

Definitions

Throughout this specification unless the text requires otherwise, the word 'comprise' and variations such as 'comprising' or 'comprises' will be understood to imply the inclusion of a stated integer or step or group of integers or steps but not the exclusion of any other integer or step or group of integers or steps.

Throughout this specification, the terms "patient" or "user" or "person" or "patient usage", when used in relation to the use of a medicament delivery device, is to be understood to refer to any person that uses a medicament delivery device.

STATEMENTS OF INVENTION

According to one aspect of the present invention, there is provided a compliance monitor for monitoring patient usage of a dry powder medicament delivery device, the medicament delivery device including:
a) a store of medicament housed within a main body portion,
b) a base portion, said base portion and said main body portion being rotatable with respect to each other,
c) a medicament dispensing means for dispensing a dose of the medicament into an inhalation chamber,
d) a mouthpiece through which the dose of medicament may be inhaled by a user,
e) a removable and replaceable cap,
and the compliance monitor including:
f) a first portion for receiving and/or retaining the base portion of the medicament delivery device,
g) a second portion for releasably securing the medicament delivery device to the first portion, thereby releasably attaching the compliance monitor to the medicament delivery device,
the arrangement and construction being such that the fitting of the second portion of the compliance monitor to the first portion of the compliance monitor does not include a screw fit.

In such an embodiment, the first and second portions of the compliance monitor may be attached to each other by any suitable means.

In one embodiment, the first and second portions of the compliance monitor may be attachable to each other by the use of a push fit.

In an alternative embodiment, the second portion of the compliance monitor may be adapted to be a "push and turn" type fitting with respect to the first portion of the compliance monitor, for example similar to a bayonet-type fitting for a light bulb.

In a further embodiment, the second portion of the compliance monitor may be attached to the first portion of the compliance monitor through a living hinge or a releasable catch.

In yet another embodiment, the second portion of the compliance monitor may be attached to the first portion of the compliance monitor by the use of magnets. Alternatively or additionally, magnets may be utilised to provide the necessary attachment between the compliance monitor and the medicament delivery device. According to another aspect of the present invention, there is provided a compliance monitor for monitoring patient usage of a dry powder medicament delivery device, the medicament delivery device including:
a) a store of medicament housed within a main body portion,
b) a base portion, said base portion and said main body portion being rotatable with respect to each other,
c) a medicament dispensing means for dispensing a dose of the medicament into an inhalation chamber,
d) a mouthpiece through which the dose of medicament may be inhaled by a user,
e) a removable and replaceable cap,
and the compliance monitor including:
f) a first portion for receiving and/or retaining the base portion of the medicament delivery device,
g) a second portion for releasably securing the medicament delivery device to the first portion, thereby releasably attaching the compliance monitor to the medicament delivery device,
the arrangement and construction being such that the fitting of the second portion of the compliance monitor to the first portion of the compliance monitor includes a push fit.

The compliance monitor may be particularly suitable for use with dry powder inhalers, for example those sold under the trade marks TURBUHALER® and TWISTHALER®. However, it is to be understood and appreciated that the invention is not to be limited to such use. For example, the compliance monitor could also be used with other dry powder medicament delivery devices, such as those used for the treatment of pain, heart conditions, erectile dysfunction, diabetes, and so on.

Any suitable medicament dispensing means may be utilised for dispensing a dose of medicament into the inhalation chamber.

For example, in the case of a dry powder inhaler sold under the trade mark TURBUHALER®, a single dose of medicament may be dispensed into the inhalation chamber when the rotatable base is rotated (with respect to the main body portion) as far as it will go in one direction, before being returned back to its original starting position. This back-and-forth action only needs to be completed once (for dispensing each dose of medicament) and the user should hear a click when this action has been completed successfully.

For the dry powder inhaler sold under the trade mark TWISTHALER®, a dose of medicament may be dispensed into the inhalation chamber when the base is rotated once with respect to the main body portion, however this rotation is automatically facilitated by the removal of the cap from the inhaler (and/or by the action of screwing the cap onto the inhaler).

For both the TURBUHALER® and the TWISTHALER® devices, the store of medicament is usually in the form of a single and solid mass housed within the main body portion of the inhaler. The rotating of the base portion with respect to the main body portion (or vice versa) causes internal scrapers to scrape a small amount of medicament from off the single mass, after which the removed medicament is directed into the inhalation chamber—in the form of a metered amount of dry powder.

The dry powder is then inhaled by the user who sucks strongly on the mouthpiece. The mouthpiece is usually located at one end of the main body, although it is envisaged that the mouthpiece could alternatively be located on the side of the main body.

One reason for including a cap with the inhaler is that the cap keeps the mouthpiece (and associated delivery channel) clean, and free from dust and grime, and also ensures no foreign objects enter the mouthpiece, which may present a choking hazard.

Furthermore, there is usually an airtight seal formed between the cap and the inhaler, and this helps to keep the medicament dry, fresh, and substantially free from atmospheric conditions such as high humidity (which can otherwise degrade the medicament or reduce its shelf life). Such air tight seals are usually provided for by a rubber or silicon sealing ring, against which the cap rests or abuts, once being attached to the inhaler.

Preferably, the compliance monitor may include a first portion for receiving and/or retaining the base portion of the medicament delivery device, and a second portion for releasably securing the medicament delivery device to the first portion, thereby releasably attaching the compliance monitor to the medicament delivery device (and/or vice versa). Preferably, the arrangement and construction may be such that the fitting of the second portion of the compliance monitor to the first portion of the compliance monitor includes a push fit.

In one embodiment, the second portion of the compliance monitor may be adapted to clip onto, or into, the first portion of the compliance monitor, for example, by the engagement of one or more complementary male and female clipping portions, housed on the second portion of the compliance monitor and the first portion of the compliance monitor, respectively (or vice versa).

In such an embodiment the first portion of the compliance monitor may include a quick release means to release the second portion of the compliance monitor from the first portion of the compliance monitor. Alternatively, the second portion of the compliance monitor may include a quick release means to release the first portion of the compliance monitor from the second portion of the compliance monitor. Such quick release means may be in the form of at least one quick release button, which serves to disengage the male and female clipping portions from each other.

In an alternative embodiment, the second portion of the compliance monitor may be adapted to be a "push and turn" type fitting with respect to the first portion of the compliance monitor, for example similar to a bayonet-type fitting for a light bulb. In such an embodiment, the amount of turn required may be minimal, whereby negligible rotation of the base portion may occur if the base portion is inadvertently rotated at the same time—whereby a dose of medicament cannot inadvertently be dispensed (or half-dispensed) when fitting the second portion of the compliance monitor to the first portion of the compliance monitor.

In a further embodiment, the second portion of the compliance monitor may be attached to the first portion of the compliance monitor through a living hinge or a releasable catch.

In yet another embodiment the first and second portions of the compliance monitor may be attachable to each other by the use of a push fit—for example similar to how plumbing or hose fittings are attached to (and/or released from) each other.

In another embodiment, the second portion of the compliance monitor may be attached to the first portion of the compliance monitor by the use of magnets. Alternatively or additionally, magnets may be utilised to provide the necessary attachment between the first and/or second portions of the compliance monitor and the medicament delivery device.

According to another aspect of the present invention, there is provided a compliance monitor for monitoring patient usage of a medicament delivery device, substantially as described above, wherein the compliance monitor includes a dose detection means for determining if a dose of medicament has been dispensed and/or if the base portion has been rotated with respect to the main body portion.

In one embodiment, the dose detection means may determine if a dose of medicament has been dispensed. For the TURBUHALER® this involves the dose detection means determining that the base portion has been rotated back and forth once with respect to the main body portion. For the TWISTHALER®, this involves the dose detection means determining that the base portion has been rotated with respect to the main body portion (or vice versa).

For the TURBUHALER®, it is envisaged that the dose detection means may also be able to determine if the base portion has been rotated only once, and in one direction (with respect to the main body portion), whereby a dose of medicament has not been properly dispensed (and instead a dose has been "half dispensed").

Any suitable dose detection means may be utilised.

For example, an optical dose detector may be utilised for detecting rotation of the base portion with respect to the main body portion. Alternatively, an electromechanical switch may be utilised, with the rotation of the base portion (and/or compliance monitor) with respect to the main body portion actuating the electromechanical switch.

In yet another embodiment, the dose detection means may be in the form of a mechanical switch.

According to another aspect of the present invention, there is provided a dose detection means for a dry powder medicament delivery device, substantially as described above, said dose detection means including:
  a) a rotor which holds the base of the dry powder medicament delivery device, the rotor being capable of rotating both ways,
  b) a torque sensor or torque switch comprising at least one leaf spring, wherein the torque sensor controls the rotation of the rotor,
  c) a switch engaged or disengaged by the movement of the rotor or the movement of the leaf spring(s).

To facilitate the fitting and removal of the cap with respect to the medicament delivery device, and for example, an interior surface of the cap may be provided with a first threaded portion, and an outside portion of the main body portion of the medicament delivery device may be provided with a complementary second threaded portion, whereby the cap may be removed and replaced, with respect to the medicament delivery device, by unthreading and threading, respectively, the first and second threaded portions with respect to each other According to another aspect of the present invention, there is provided a compliance monitor for monitoring patient usage of a medicament delivery device, substantially as described above, wherein the compliance monitor includes a cap detection means for determining if the cap is attached to the medicament delivery device or is removed from the medicament delivery device.

Any suitable cap detection means may be utilised.

For example, the cap detection means may be in the form of an electromechanical, optical or pressure switch which is actuated, and de-actuated, when the cap is attached to, and removed from, the medicament delivery device, respectively.

Furthermore, the dose detection means and/or the cap detection means may preferably be adapted, or able, to differentiate between when a user dispenses a dose of medicament normally, as compared to when a dose of medicament is inadvertently dispensed when the cap is being removed or replaced.

According to another aspect of the present invention, there is provided a compliance monitor for monitoring patient usage of a medicament delivery device, substantially as described above, wherein the action of screwing the cap to the main body portion has the effect of moving the medicament delivery device within the second portion of the compliance monitor, and in a direction away from the first portion of the compliance monitor, and it is this action which causes the cap to be detected as being attached.

According to another aspect of the present invention, there is provided a compliance monitor for monitoring patient usage of a medicament delivery device, substantially as described above, wherein the action of unscrewing the cap from the main body portion has the effect of moving the medicament delivery device within the second portion of the compliance monitor, and in a direction towards the first portion of the compliance monitor, and it is this action which causes the cap to be detected as having been removed.

According to another aspect of the present invention, there is provided a compliance monitor for monitoring patient usage of a medicament delivery device, substantially as described above, wherein the cap detection means and/or the dose detection means can determine if the user dispenses, or attempts to dispense, a dose of medicament when the cap is attached to the medicament delivery device.

While a user of the TURBUHALER® or TWISTHALER® device is usually unable to actually dispense a dose of medicament when the cap is attached to the device, the user may nonetheless believe they have dispensed a dose of medicament by simply attempting to rotate the base portion with respect to the main body portion. The user may thereafter remove the cap and inhale from the mouthpiece, inadvertently believing they have inhaled a dose of medicament.

And so it may be important to be able to detect when the user attempts to dispense a dose of medicament when the cap is still attached to the medicament delivery device, for example for re-training purposes, or simply to determine if the user has not in fact received their dose of medicament.

According to another aspect of the present invention, there is provided a compliance monitor for monitoring patient usage of a medicament delivery device, substantially as described above, wherein the compliance monitor includes a device detection means for detecting if the compliance monitor is attached to, and/or removed from, the medicament delivery device.

In one embodiment, the device detection means may be located within the first portion of the compliance monitor, whereby the presence of the medicament delivery device is detected as soon as the base portion of the medicament delivery device is received and/or retained by the first portion of the compliance monitor.

In an alternative embodiment, the device detection means may detect the presence of the medicament delivery device when the second portion of the compliance monitor is attached to the first portion of the compliance monitor.

The device detection means may be in the form of an electromechanical or pressure switch which is actuated, and de-actuated, when the device is attached to, and removed from, the medicament delivery device, respectively.

Alternatively, and/or additionally, the device detection means may detect the removal of the medicament delivery device from the compliance monitor when the second portion of the compliance monitor is removed from the first portion of the compliance monitor.

According to another aspect of the present invention, there is provided a compliance monitor for monitoring patient usage of a medicament delivery device, substantially as described above, wherein the compliance monitor is only operable, or in operation, when the second portion of the compliance monitor has been attached to the first portion of the compliance monitor.

In such an embodiment, and for example, the compliance monitor may be adapted to only record or log any rotation of (or attempts to rotate) the base portion of the medicament delivery device with respect to main body portion (and/or any rotation of the first portion of the compliance monitor with respect to the base portion of the medicament delivery device), when the second portion of the compliance monitor has been attached to the first portion of the compliance monitor.

Hence, this ensures that any compliance monitoring of the medicament delivery device only occurs once the compliance monitor has been attached to the medicament delivery device. To facilitate this, a suitable algorithm may be devised and incorporated within the compliance monitor, or the ECM of the compliance monitor (see below).

In addition, the compliance monitor may be adapted to record or log a correct use when the correct rotation of the base portion of the medicament delivery device with respect to the main body occurs (i.e. rotation one way and then back until a click is heard for TURBUHALER® or one way rotation for the main body of TWISTHALER® with respect to its base portion).

Further, the compliance monitor may be adapted to record or log an error use, for example when TURBUHALER® cap is removed but the base of the inhaler is rotated only one way.

Further still, the compliance monitor may be adapted to record or log an error use when the cap is removed but no dose is dispensed.

Preferably, the compliance monitor may further include an electronics control module (ECM), the ECM being adapted to monitor and/or manipulate and/or store and/or transmit all compliance data gathered, relating to the patient usage of the medicament delivery device.

The use of ECM's, in conjunction with compliance monitors for medicament delivery devices, are well known, and it is not intended therefore to describe them in any significant detail herein.

The ECM and/or the compliance monitor be powered by any suitable means, for example a battery (rechargeable or replaceable), a kinetic charger, or by solar power.

The compliance monitor and/or the ECM may be able to monitor for any type of non-dose counting information relating to the operation of the medicament delivery device and/or patient usage of the medicament delivery device. For example, the ECM may include a real time clock (or be in electronic communication with one) to enable the compliance monitor to record a date and time for each dose of medicament dispensed.

Furthermore, and for example only, the compliance monitor and/or the ECM may also be able to monitor criteria such as geographical location, inhalation rate, temperature, humidity, the orientation of the medicament delivery device, the condition of the medicament, the amount of medicament left, the condition of the battery or whether it is installed, the flow or pressure of the user's inhalation, an audio sensor for detecting inhalation or for determining if the main body portion has been rotated with respect to the base portion, and so on. To this effect the ECM may be connected to a GPS, audio or optical inhalation sensor, thermistor sensor or accelerometer.

The compliance monitor and/or the ECM may also include a communication device for transmitting the compliance data. In one embodiment, this may be in the form of, or provided for, by a USB port located on or within the compliance monitor. Alternatively and/or additionally, the compliance monitor and/or ECM may be provided with a wireless transmitter and/or a wireless transceiver to be able to transmit and/or receive data respectively. The data may be transmitted to a remote computer server or to an adjacent electronic device such as a smart phone.

The compliance monitor may also include a screen such as a LCD or LED screen where any or all information relating to use of the medicament delivery device may be displayed.

The compliance monitor may also include a number of user buttons so that a user can operate and/or change the settings of the compliance monitor.

An example of a compliance monitor, used in conjunction with an ECM and/or transmitter can be found in our U.S. Pat. No. 8,424,517 and our US Patent Publication No. 2014/0000598 (the contents of which are incorporated herein by reference).

Preferably, the ECM may utilise the compliance data gathered to determine if the user has used the medicament delivery device correctly and/or incorrectly. This may be achieved by incorporating an appropriate algorithm(s) within the ECM to analyse the compliance data gathered and/or to draw an appropriate conclusion.

Furthermore, the compliance monitor may also include indication means to alert the user if to any event, or if the ECM determines that the user has used the medicament delivery device correctly and/or incorrectly.

The indications means may be in the form of a visual and/or audio and/or vibrational indicator. For example, the indication means may be in the form of a visual display on an LCD screen and/or a flashing light(s) and/or an audible alert and/or by vibrating the compliance monitor.

Furthermore, different indication means may be utilised for indicating different events. For example, a continuous red light may indicate that the compliance monitor is operative; a flashing green light may indicate that a dose has been dispensed and/or inhaled correctly; a continuous orange light may indicate that the compliance monitor is currently transmitting or receiving data wirelessly; a flashing blue light may indicate that a dose has not been correctly dispensed and/or inhaled, and so on.

Preferred Embodiments

The description of a preferred form of the invention to be provided herein, with reference to the accompanying drawings, is given purely by way of example and is not to be taken in any way as limiting the scope or extent of the invention.

DRAWINGS

Figure 2:
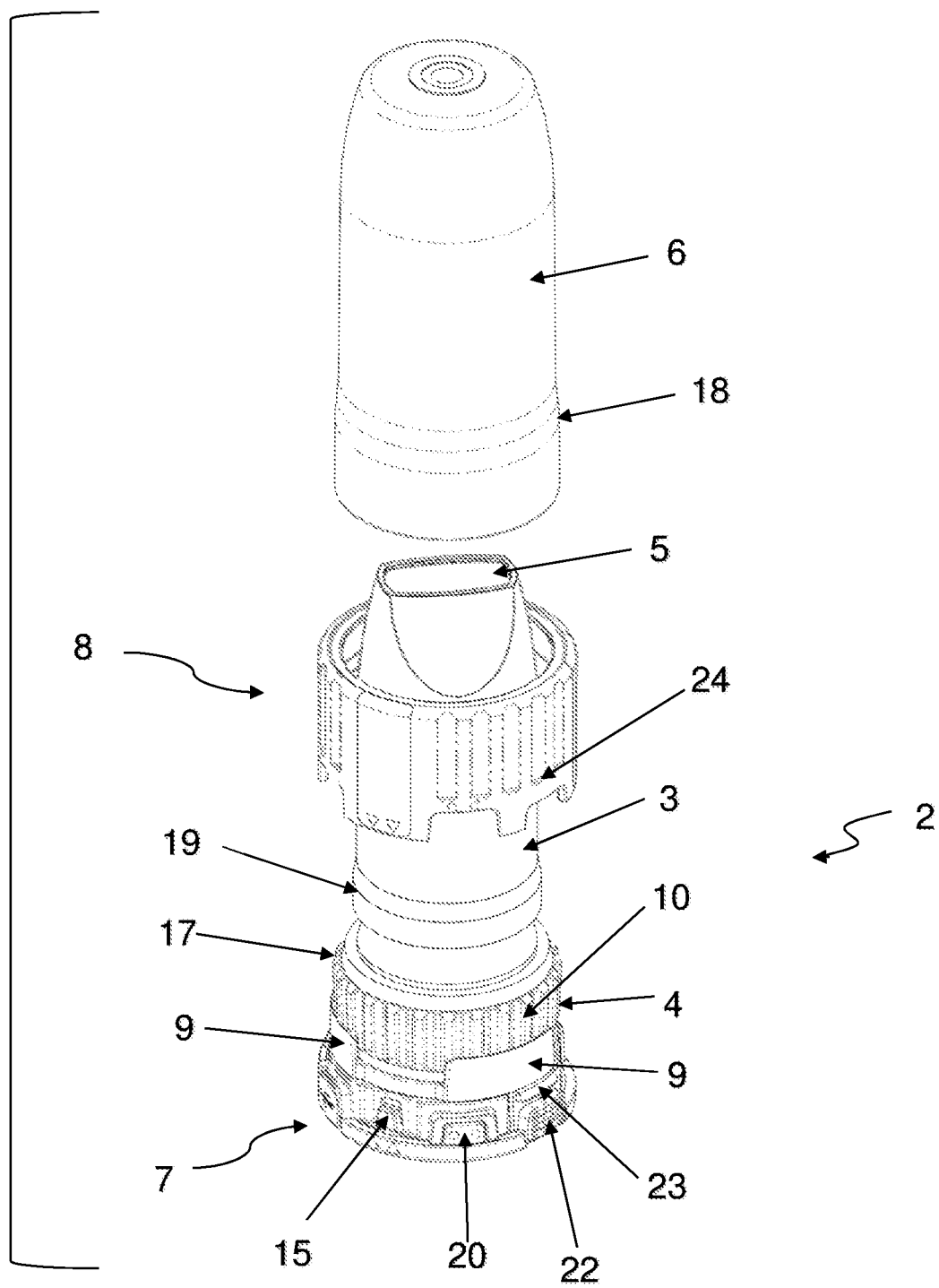
Figure 3:
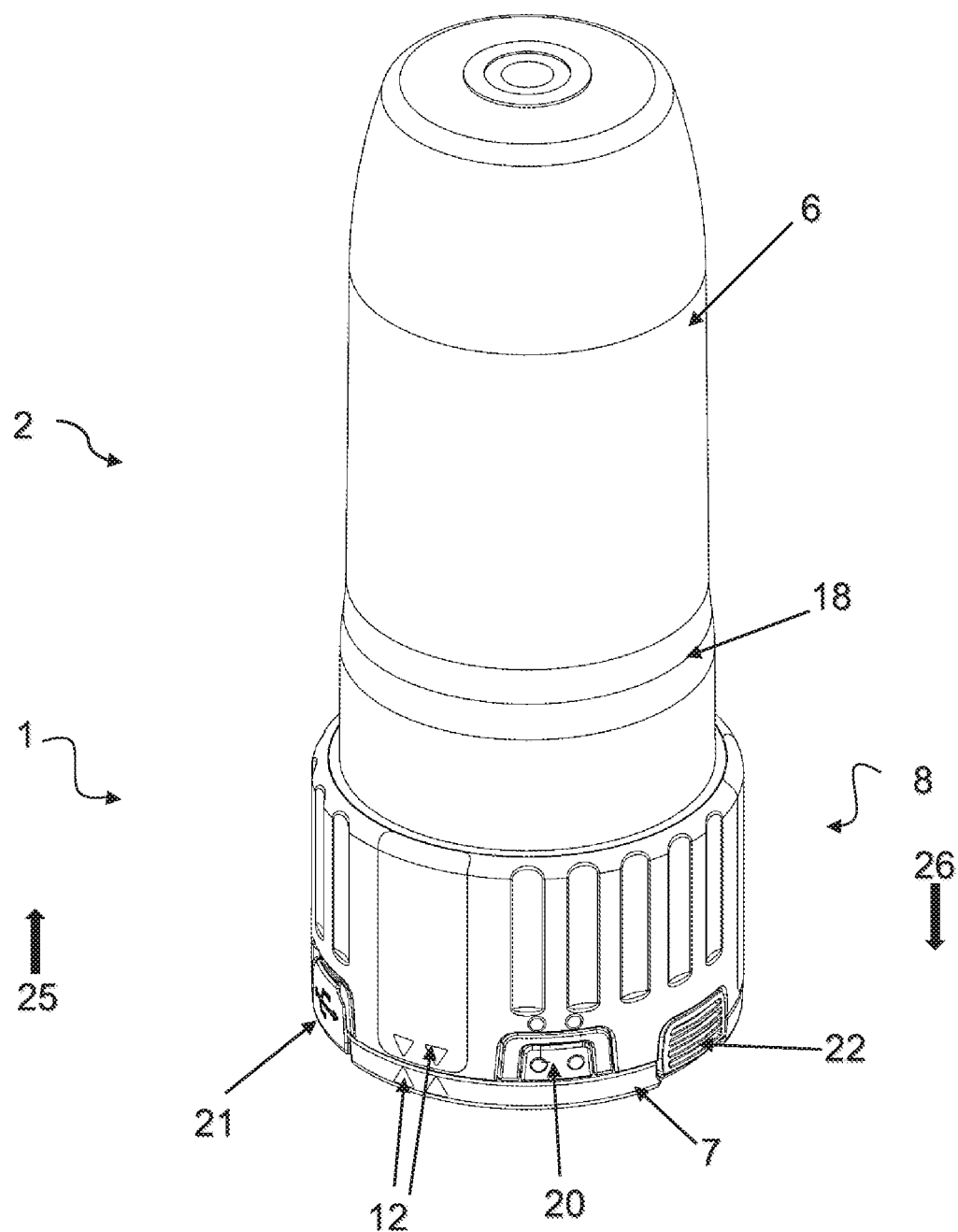
Figure 4:
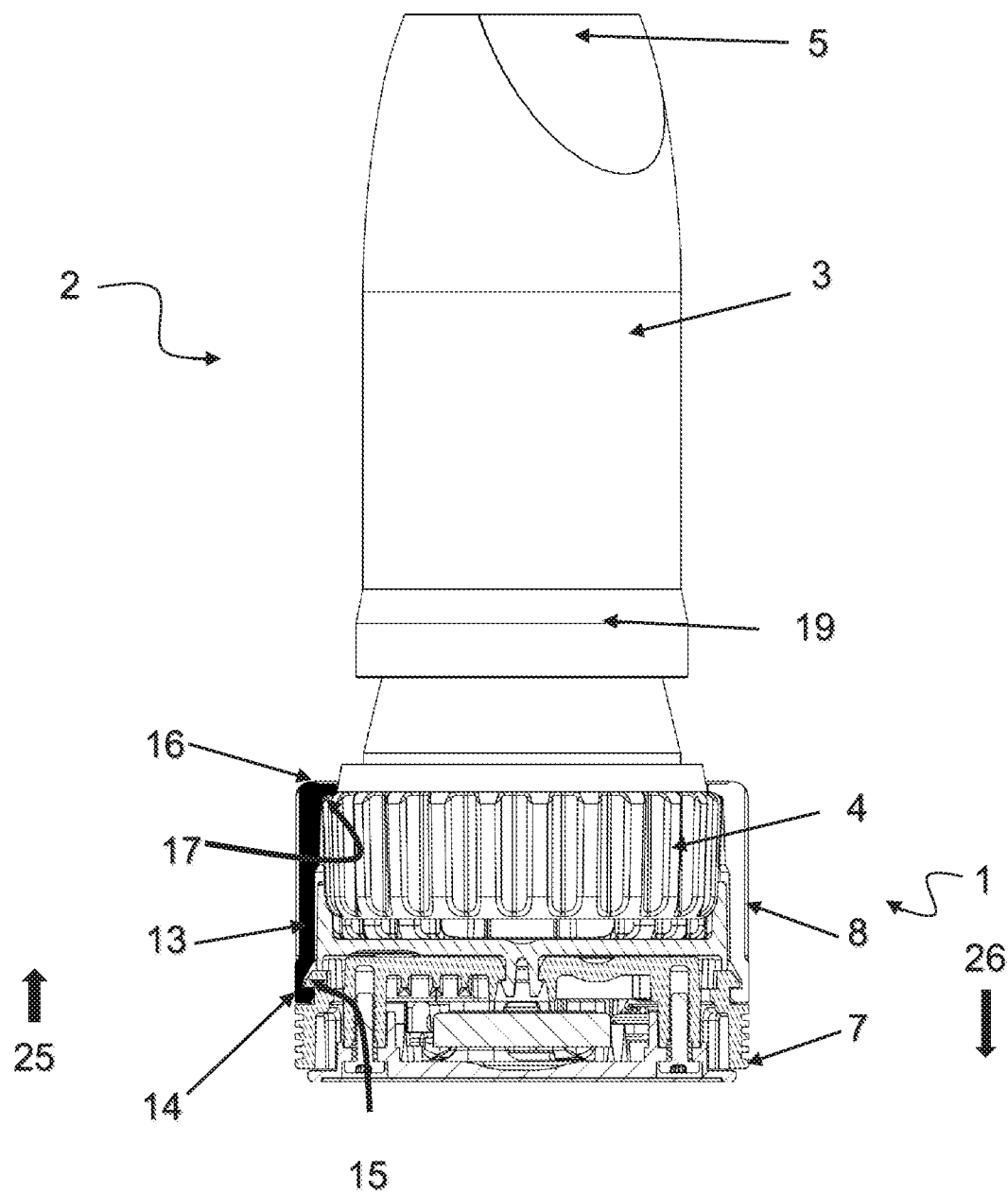
Figure 5A:
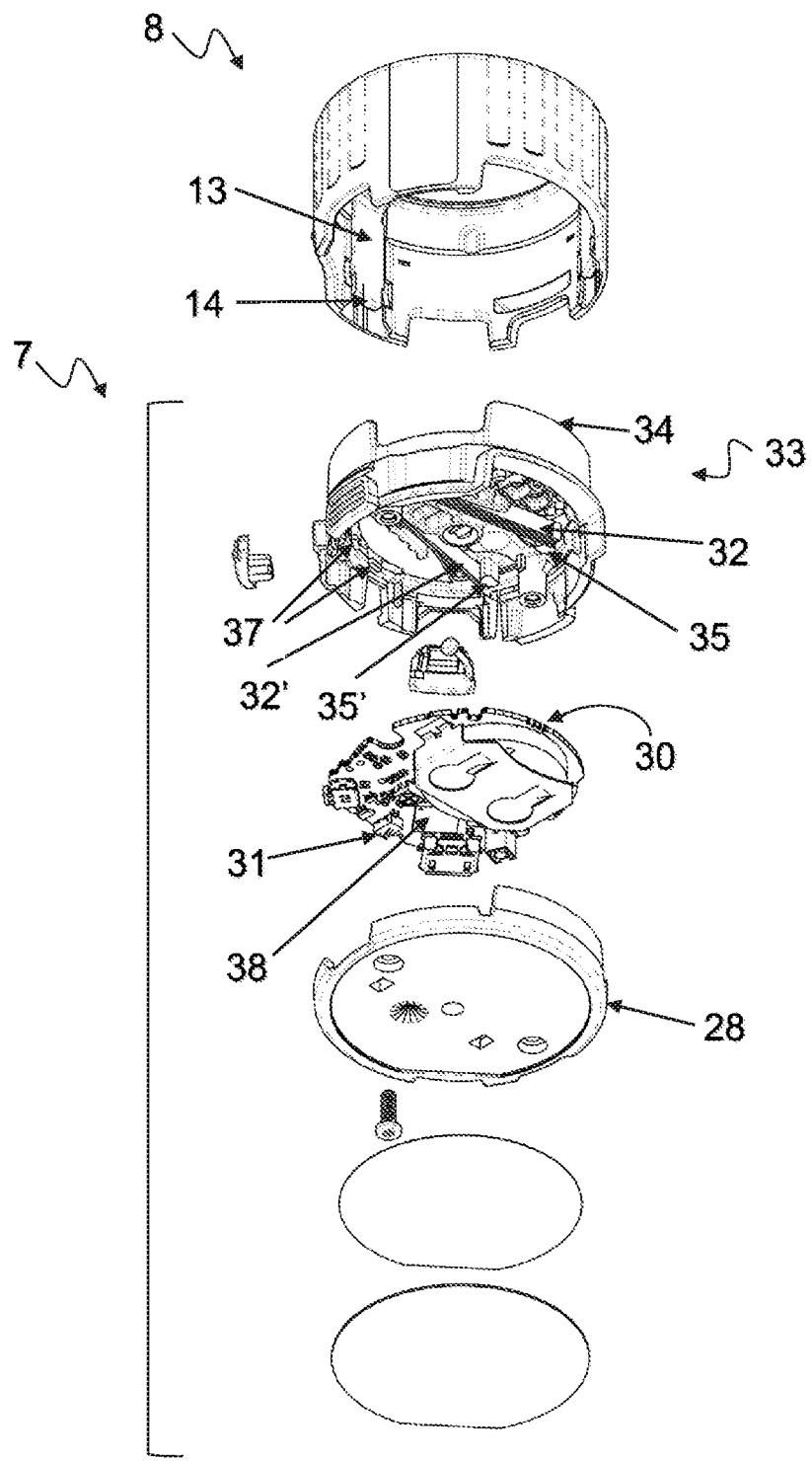
Figure 5B:
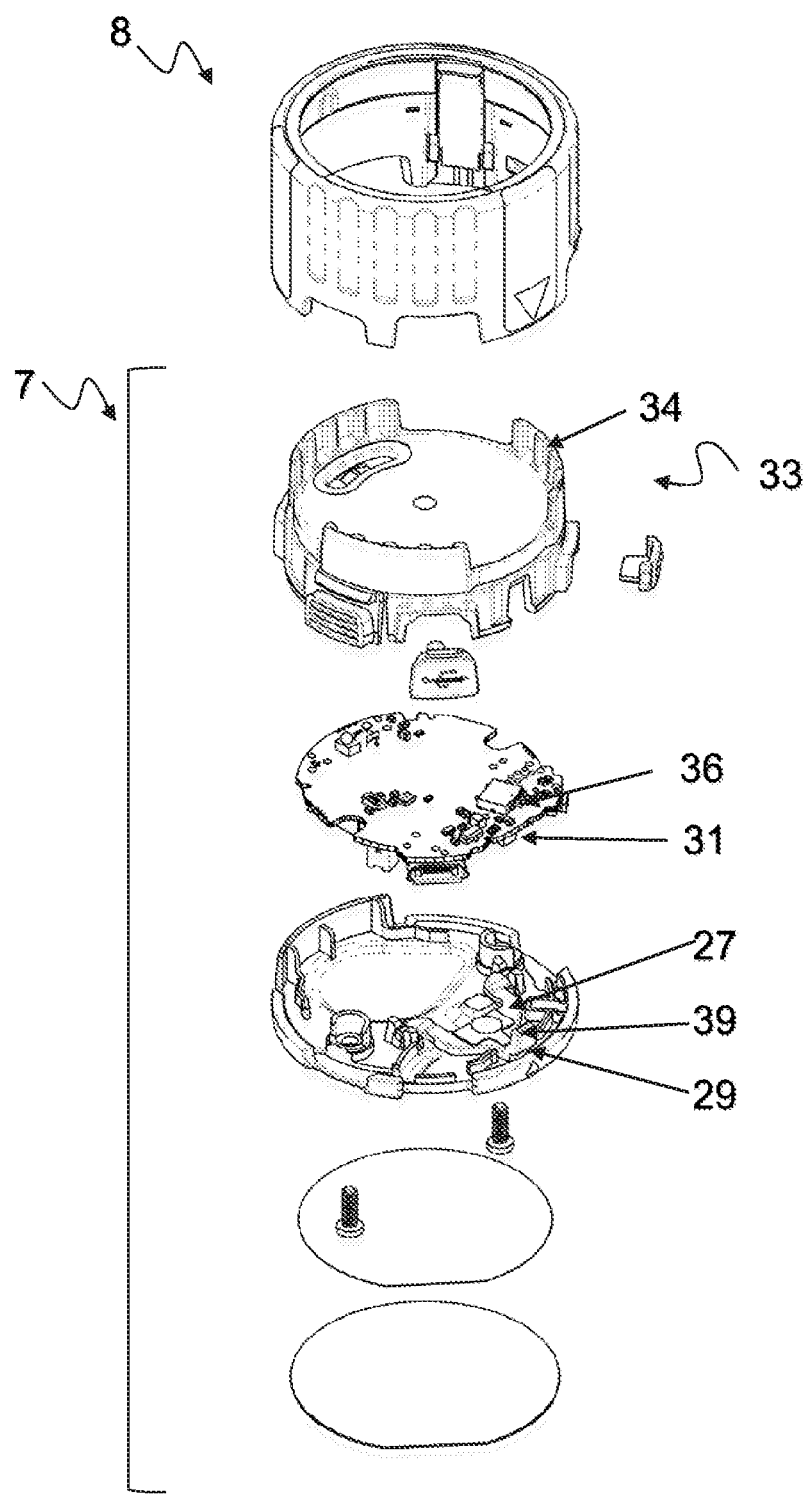

FIG. 1: is an exploded view of one possible embodiment of a compliance monitor for monitoring patient usage of a dry powder medicament delivery device, FIG. 2: is a partially exploded view of the embodiment illustrated in FIG. 1, showing how the compliance monitor is fitted to the medicament delivery device, FIG. 3: is a view of the embodiment illustrated in FIG. 2, with a cap fitted to the medicament delivery device, FIG. 4: is a cross-sectional side view of one embodiment of the compliance monitor, when fitted to the medicament delivery device (but with the cap removed), as illustrated in FIG. 3, FIG. 5A: is an inverted exploded view of one embodiment of the compliance monitor, showing angled views of each component of the compliance monitor, and FIG. 5B: is an upright exploded view of the embodiment illustrated in FIG. 5A.

DESCRIPTION OF PREFERRED EMBODIMENTS

Having regard to the drawings there is shown a compliance monitor, generally indicated by arrow 1.

The compliance monitor 1 is used for monitoring patient usage of a dry powder inhaler, generally indicated by arrow 2. The dry powder inhaler 2 is a TURBUHALER®, which is manufactured and marketed by AstraZeneca AB.

The inhaler 2 includes a store of medicament (not shown) which is housed within a main body portion 3. The inhaler 2 also includes a rotatable base portion 4, which is rotatable with respect to the main body portion 3. The inhaler 2 also includes a mouthpiece 5, through which a dose of medicament may be inhaled by a user. Also included is a removable and replaceable cap 6.

The inhaler 2 also includes a medicament dispensing means (not shown) for dispensing a dose of the medicament into an inhalation chamber (not shown).

The store of medicament is in the form of a single and solid mass, housed within the main body portion 3, and the rotating of the base portion 4 with respect to the main body portion 3 causes internal scrapers (not shown) to scrape a small amount of medicament from off the single mass, after which the removed medicament is directed into the inhalation chamber—in the form of a metered amount of dry powder.

The dry powder is then inhaled by the user who sucks strongly on the mouthpiece 5.

The internal workings of the inhaler (not shown) are usually configured to create an enhanced internal airflow when the user is sucking on the mouthpiece 5—which forces the dry powder medicament out through the mouthpiece 5, and into the mouth of the user, under significant pressure. These internal workings of the inhaler 2 therefore serve to ensure that a maximum amount of the dry powder medicament reaches, and/or is deposited in, the airways and/or lungs of the user.

The compliance monitor 1 includes a first portion 7 for receiving and retaining the base portion 4 of the inhaler 2 and a second portion 8 for releasably securing the inhaler 2 to the first portion 7, thereby releasably attaching the compliance monitor 1 to the inhaler 2.

The arrangement and construction is such that the fitting of the second portion 8 of the compliance monitor 1 to the first portion 7 of the compliance monitor 1 includes a push fit (as shall be described in more detail hereinafter).

The compliance monitor 1 may be attached to the inhaler 2 as follows.

Firstly, the cap 6 is removed from the inhaler 2.

Secondly, the base portion 4 of the inhaler 2 is placed within the first portion 7 of the compliance monitor 1 (best illustrated in FIG. 2). The base portion 4 is located by, and/or retained within, the first portion 7 by the upwardly projecting flanges 9 (see FIG. 1).

Furthermore, the base portion 4 includes external serrations 10, and the interior surfaces of the flanges 9 contain complementary serrations 11. The serrations 10 and 11 interlock with each other in such a way that a rotation of the first portion 7 also causes a like rotation of the base portion 4. That is, the first portion 7 and the base portion 4 move (rotate) as one.

Once the base portion 4 has been placed within the first portion 7, the second portion 8 of the compliance monitor 1 may then be fitted to the first portion 7 to thus releasably attach the compliance monitor 1 to the inhaler 2. This is achieved by placing the second portion 8 over the mouthpiece 5, and sliding the second portion 8 down towards the first portion 7, as illustrated in FIG. 2.

Both the first portion 7 and the second portion 8 include alignment means in the form of arrows 12 (best illustrated in FIGS. 1 & 3) and/or embossed dots on button 20 and on second portion 8, in position directly above button 20 (indicated by arrow 20'), so that the second portion 8 can be orientated correctly prior to being fitted to the first portion 7.

Once aligned correctly, the first portion 7 of the compliance monitor 1 is then fitted or attached to the second portion 8 of the compliance monitor (or vice versa) by pushing the two portions 7, 8 together. That is, the fitting of the first portion 7 to the second portion 8 includes a push fit.

To facilitate this, the first portion 7 includes two fastening clips 23, which are formed on substantially opposite sides of the first portion 7 (only one fastening clip 23 is shown in FIGS. 1 and 2). As the second portion 8 is slid down and engaged with the first portion 7, each fastening clip 23 clips into a corresponding retaining slot (not shown) formed on the inside surface of the second portion 8, in the region indicated by arrow 24. Once the fastening clips 23 have engaged with these slots, the first and second portions are thus (releasably) connected, and hence the compliance monitor 1 is thereby (releasably) attached to the inhaler 2.

The first portion 7 of the compliance monitor 1 also includes a quick release means to enable the removal of the second portion 8 from the first portion 7 (and thus to release the compliance monitor 1 from the inhaler 2. The quick release means are in the form of two quick release buttons 22 (only one is shown) which are positioned directly below the two fastening clips 23. Pushing both quick release buttons 22 together serves to disengage the fastening clips 23 from the slots, and hence the second portion 8 may thereafter be removed from the first portion 7.

The engagement of the fastening clips 23 with the retaining slots may (optionally) serve as a device detection means, for example by closing an electronic circuit, to thus record that the compliance monitor 1 is attached to the inhaler 2.

Likewise, the disengagement of the fastening clips 23 from the retaining slots may (optionally) open the same electronic circuit to thus record that the compliance monitor 1 has been removed from the inhaler 2.

Having regard to FIG. 1, the inside surface of the second portion 8 includes three sliding clips 13,13' and 13" which are spaced apart equally, that is by 120° (only two sliding clips 13,13' can be properly seen). All three sliding clips 13, 13' and 13" are able to slide up and down within the inside surface of the second portion 8 (with approximately 2-4 mm total up-down movement possible).

One sliding clip 13 is illustrated in exploded view in FIG. 1.

The upper portion of all three sliding clips 13, 13' and 13" also include a lip 16, and these three lips 16 are all adapted to clip over and/or engage with the top shoulder 17 of the base portion 4—once the second portion 8 has been attached to the first portion 7. This is best illustrated in FIG. 4.

The sliding clip 13 includes a lower portion 14 which is adapted to clip into (or onto) the complementary clip 15, which is housed on the first portion 7. The complementary clip 15 is able to flex slightly so that as the second portion 8 is pushed into or onto the first portion 7, the lower portion 14 is able to slide over, or push past, the complementary clip 15, in order to engage the lower portion 14 with the complementary clip 15.

The sliding clip 13 is the only one of the three sliding clips 13, 13' and 13" that attaches to the first portion 7, via the engagement of the lower portion 14 and the complementary clip 15. This arrangement is best illustrated in FIG. 4, where the attachment of the complementary clip 15 to the lower portion 14 is shown (the sliding clip 13 is represented as a solid black portion). The lips 16 of other two sliding clips 13' and 13" are however adapted to attach to the top shoulder 17 of the base portion 4, however these two sliding clips 13' and 13" do not have a lower portion 14 and nor are the lower portions of these two sliding clips 13' and 13" attached to the first portion 7.

The engagement of the lower portion 14 and the complementary clip 15 may close or open an electromechanical switch (not shown), which serves as a device detection means to detect if and/or when the inhaler 2 is fitted to the compliance monitor 1. Likewise, the removal of the second portion 8 from the first portion 7 may open the same electromechanical switch, which serves to detect if and/or when the inhaler 2 is removed from the compliance monitor 1.

Once the second portion 8 has been attached to the first portion 7, the cap 6 may then be re-attached to the inhaler 2.

The interior surface of the cap 6 is provided with a first threaded portion 18 (shown as a dotted line), and the outside of the main body portion 3 is provided with a complementary second threaded portion 19, whereby the cap 6 may be attached to the inhaler 2 by placing it over the main body portion 3, and screwing the first threaded portion 18 and the second threaded portion 19 together. Likewise, the cap 6 may be removed from the inhaler 2 by unscrewing the first threaded portion 18 and the second threaded portion 19 from each other, and subsequently removing the cap 6.

FIG. 3 illustrates when the cap 6 has been attached to the inhaler 2 (with the compliance monitor 1 also fitted to the inhaler 2) and FIG. 4 illustrates when the cap 6 has been removed from the inhaler 2 (but with the compliance monitor 1 still fitted to the inhaler 2).

The action of screwing the cap 6 to the main body portion 3, until it is tight, has the effect of slightly moving the base portion 4 of the inhaler 2 within the second portion 8, and in a direction away from the first portion 7 (as indicated by arrow 25). This occurs because the action of tightening the screw cap 6 automatically pulls at the base portion 4, and because the base portion 4 is retained by the lips 16 of the sliding clips 13, 13', 13", the base portion 4 moves slightly within the second portion 8, by virtue of the movement of the sliding clips 13, 13', 13"—and in a direction away from the first portion 7.

Furthermore, this action serves as a cap detection means because it has the effect of causing the cap 6 to be detected as being attached. That is, and with respect to FIG. 4, this action results in the lower portion 14 of the sliding clip 13 pulling on the complementary clip 15, which closes an electromechanical switch (not shown), which thus records or detects the cap 6 as being attached.

Likewise, the removal of the cap 6, by unscrewing the cap 6 with respect to the main body portion 3, has the effect of slightly moving the base portion 4 of the inhaler 2 within the second portion 8, and in a direction towards from the first portion 7 (an opposite direction to arrow 25, as indicated by arrow 26). Hence, the same electromechanical switch is opened, thus recording or detecting the cap 6 as being removed.

An alternative arrangement of the sliding clip 13 is shown in FIGS. 5A and 5B. The first portion 7 houses in its base 28 a hinged lever sensor 27 with a tip 39. The hinged lever sensor 27 is supported by a spring or a foam pad placed in position 29. When the first portion 7 is not connected to the second portion 8, the tip 39 of the hinged lever sensor 27 is lifted and comes into contact with a microswitch 31 on the circuit board 30.

When the second portion 8 is fitted onto first portion 7, the lower portion 14 of sliding clip 13 rests on the tip 39 of the hinged lever sensor 27 and pushes the hinged lever sensor 27 towards the base 28 of the first portion 7 and away from the microswitch 31, thereby disengaging the microswitch 31.

When the inhaler 2 is inserted into the first portion 7 and the second portion 8 is attached to the first portion 7 thereby releasably attaching the compliance monitor 1 to the inhaler 2, the position of sliding clip 13 remains unchanged in relation to the complementary clip 15 of the hinged lever sensor 27, and the microswitch 31 is disengaged.

When the cap 6 is screwed onto the inhaler 2, held within the compliance monitor 1, the sliding clip 13 (as well as sliding clips 13' and 13") is pulled up away from the first portion 7, as described above. This action releases the pressure of sliding clip 13 on the complementary clip 15 of the hinged lever sensor 27. The spring or foam pad 29 pushes the hinged lever sensor 27 away from the base 28 of the first portion 7 and towards the microswitch 31, thereby engaging the microswitch 31. The screwing of the cap 6 onto the inhaler 2 is thereby detected and recorded by the electronics control module (described below) (ECM). The reverse occurs when the cap 6 is removed from the inhaler 2. Unscrewing of the cap 6 from the inhaler 2 releases the sliding clip 13 which, in turn, rests on the complementary clip 15 of the hinged lever sensor 27 and pushes the hinged lever sensor 27 towards the base 28 of the first portion 7 and away from microswitch 31, thereby disengaging the microswitch 31. The unscrewing of the cap 6 from inhaler 2 is thereby detected and recorded by the ECM (described below).

Once the compliance monitor 1 has been fitted to the inhaler 2 (and this has been detected by the device detection means, as described previously), a dose of medicament may be dispensed as follows.

Firstly, the cap 6 is unscrewed from the main body portion 3 of the inhaler 2, and this action is detected by the cap detection means, as described previously.

The compliance monitor 1 is then rotated back and forth once with respect to the main body portion 3, which has the effect of rotating the base portion 4 back and forth once with respect to the main body portion 3. As described previously, this results in a metered dose of dry powder medicament being placed within the inhalation chamber, from where it may be inhaled by a user—by the user sucking strongly on the mouthpiece 5. The cap 6 may then be screwed back onto the main body portion 3 of the inhaler 2—and again this action is detected by the cap detection means, as described previously.

The compliance monitor 1 also includes dose detection means for determining if a dose of medicament has been dispensed and/or if the base portion 4 has been rotated with respect to the main body portion 3 in a way which is required to dispense a dose of medication.

The dose detection means of the invention comprises a calibrated torque detection system, embedded into the housing of the first portion 7. When the force required to correctly rotate the base portion 4 in relation to the main body 3 of the inhaler 2 is used, the torque system actuates an electromechanical switch. The 'on' signal is then recorded by the ECM (described below). Rotation of the base portion 4 in the opposite direction (until a click is heard) also requires a pre-set torque. If that correct level of torque for the specific device is used, then the torque system actuates an electromechanical switch and, again, the 'on' signal is recorded by the ECM. The ECM may, for example and without limiting other methods, be calibrated to: (a) confirm and log that a dose was correctly dispensed if both 'on' signals are detected, (b) confirm and log that a dose was incorrectly dispensed if the second 'on' signal is not detected, (c) measure the time delay between the first switch actuation and the second actuation and if the delay between them exceeds a pre-set value, confirm and log that the dose was incorrectly dispensed and/or (d) detect and time-out occurrences where the device is jammed in one position.

In one preferred embodiment, the dose detection means is provided for by the presence of leaf springs 32, 32' (FIG. 5A) housed within the first portion 7 of the compliance monitor 1. The pressure of rotating the compliance monitor 1 with respect to the main body portion 3 (to thereby rotate the base portion 4 with respect to the main body portion 3) results in the leaf springs actuating an electromechanical switch (not shown).

In one embodiment the dose detection means detects doses as follows. The compliance monitor 1 is fitted onto the inhaler 2 and the cap 6 is removed from the main body portion 3. Holding the main body portion 3 of the inhaler 2, the patient turns the compliance monitor 1 and thereby the base portion 4 of the inhaler 2 one way (e.g. anticlockwise) and then the other way (clockwise in this instance) until a click is heard. The click informs the patient that the inhaler 2 is loaded with the dose. The first portion 7 of the compliance monitor 1 consists of the base 28, circuit board 30, leaf springs 32 and 32' held within mid-housing 33 and rotor 34. The rotor 34 is attached to the mid-housing 33 in a way which allows the rotor 34 to turn either way in relation to the mid-housing 33. Protrusions 35 and 35' located on the base of the rotor 34 are positioned so that in a 'rest' position they abut the leaf springs 32 and 32' held within the mid-housing 33. When the compliance monitor 1 and base portion 4 is turned one way in relation to the main body portion 3 to the point of resistance, the resistance of the base portion 4 causes the rotor 34 to move separately from the rest of the compliance monitor 1. This movement causes protrusions 35 or 35' (depending on the direction of the turn) to push the leaf spring 32 or 32' respectively. When the force with which the leaf springs 32 or 32' are pushed exceeds the pre-set torque level, the rotor 34 turns in relation to mid-housing 33. Movement of the rotor 34 causes teeth 37 to engage switch 36. In an alternative embodiment, the leaf spring to which the required force is applied moves and engages the switch 36 on the circuit board 30. Each leaf spring 32, 32' may have its own switch or a two-way directional switch may be placed between the leaf springs. Other positions of the switch 36 on the circuit board 30 and other methods of activating the switch via the movement of the rotor are also possible. The leaf springs 32, 32' may be adjusted so that the torque required to engage the switche(s) differs, depending on the torque required to dispense a dose of the medicament from inhaler 2.

In other embodiments of the dose detection means, other spring systems could be used.

In another preferred embodiment, the spring system may consist of one leaf spring positioned on the side nearest the rotation required to dispense the medicament. One leaf spring based torque system may include one or more protrusions required to detect rotation either one way or both ways.

In one embodiment, the dose detection means may be set up so as to only record a dose as having been dispensed when the compliance monitor 1 (and therefore base portion 4) has been rotated back and forth once with respect to the main body portion 3 (which is the usual way of dispensing a dose for the TURBUHALER® device illustrated). Hence, the dose detection means serves to detect and/or record every time a dose of medicament has been dispensed.

Additionally, the dose detection means may be set up so as to also detect and/or record when the compliance monitor 1 (and therefore base portion 4) has only been rotated once, and in one direction, with respect to the main body portion 3. Many users inadvertently or erroneously believe that a dose of medicament has been dispensed by such an action, whereas a dose will only be dispensed once this action has been completed twice (that is, forward and then back). Hence, and in such an embodiment, the dose detection means can determine incorrect usage of the inhaler 2 by a user, that is, an incorrect technique for dispensing a dose of medicament.

Additionally, the dose detection means may also be set up so as to detect and/or record each time that an attempt is made to rotate the compliance monitor 1 (and therefore the base portion 4) with respect to the main body portion 3, when the cap 6 is still attached (as detected or recorded by the cap detection means). It is not possible to dispense a dose of medicament with the cap 6 still attached. However, a user may nonetheless erroneously believe that they have dispensed a dose of medicament, and they may subsequently remove the cap 6 and suck on the mouthpiece 5, believing that they have received a dose of medicament. Hence, the dose detection means serves to detect and/or record such erroneous techniques. For example, such erroneous use of the inhaler 2 may be detected by the compliance monitor 1 including an electronic pressure switch, which may closed when a sufficient and predetermined rotational pressure is applied to it (even if the rotation of the base portion 4 is not actually permitted, for example because the cap 6 is still attached).

Furthermore, the dose detection means and/or the cap detection may be adapted, or able, to differentiate between when a user dispenses a dose of medicament normally, as compared to when a dose of medicament is inadvertently dispensed when the cap is being removed or replaced. This may be achieved, for example, by determining that the timing of the dispensing of a dose of medicament was at substantially the same time as the cap being removed or replaced.

Preferably, the compliance monitors 1 may be electronic, and accordingly, the compliance monitor 1 may further include an electronics control module (ECM) 38, with the ECM being adapted to monitor and/or manipulate and/or store and/or transmit all compliance data gathered, relating to the patient usage of the medicament delivery device.

The use of ECM's, in conjunction with compliance monitors for medicament delivery devices, are well known, and it is not intended therefore to describe them in any significant detail herein.

The compliance monitor 1 and/or the ECM 38 are powered by a battery, and either a rechargeable or replaceable battery may be used.

The ECM 38 utilises the compliance data gathered to determine if the user has used the inhaler correctly and/or incorrectly.

The compliance monitor 1 also includes indication means (not shown) to indicate an event and/or to alert the user if the ECM 38 determines that the user has used the inhaler correctly and/or incorrectly.

For example, the indication means may be utilised to alert the user if they have only rotated the compliance monitor 1 (and therefore the base portion 4) once, and in one direction.

Furthermore, the indication means may be utilised to alert the user if they have attempted to dispense a dose of medicament with the cap 6 still attached.

The indication means may be in the form of a visual and/or audio and/or vibrational indicator.

The compliance monitor 1 also includes a multi-function button 20 for monitoring several aspects of the compliance monitor 1. For example, pushing the button 20 once may result in a green light showing if the compliance monitor 1 is fitted to the inhaler 2 correctly, and in normal working order. Conversely, a red light may indicate a problem. Pushing the button 20 twice may provide for another aspect of the compliance monitor to be checked or reported, and furthermore pushing and holding the button 20 may result in yet another function or check being done.

The embodiments of the compliance monitor 1 and/or the ECM 38 described herein may be able to monitor for any type of non-dose counting information relating to the operation of the inhaler 2, and/or patient usage of the inhaler 2. For example, the ECM may include a real time clock (or be in electronic communication with one) to enable the compliance monitor 1 to record a date and time for each dose of medicament dispensed. The EMC 38 may be calibrated to compare the actual doses dispensed against the table of pre-set dosage times and, if the dose is not dispensed at the pre-set time, alert the user that a dose is due.

Furthermore, and for example only, the compliance monitor 1 and/or the ECM 38 may also be able to monitor criteria such as geographical location, temperature, humidity, the orientation of the inhaler 2, the condition of the medicament, the amount of medicament left, the condition of the battery or whether it is installed, the flow or pressure of the user's inhalation, an audio sensor for detecting inhalation or for determining if the main body portion has been rotated with respect to the base portion, and so on.

The compliance monitor 1 and/or the ECM 38 may also include a communication device for transmitting the compliance data.

In one embodiment, this may be in the form of, or provided for, by a USB port 21 located on the first portion 7 of the compliance monitor 1.

Alternatively and/or additionally, the compliance monitor 1 and/or ECM 38 may be provided with a wireless transmitter and/or a wireless transceiver to be able to transmit and/or receive data respectively. The data may be transmitted to a remote computer server or to an adjacent electronic device such as a smart phone or electronic tablet.

One advantage of using of the compliance monitor 1, in conjunction with the inhaler 2, is that the compliance monitor 1 allows for all correctly dispensed doses to be detected and/or recorded.

Furthermore, the compliance monitor 1 can detect and/or record when the user does not dispense a dose of medicament correctly.

The gathering of such compliance data is important, not just for ascertaining medicament compliance generally, but for also being able to determine incorrect usage of the inhaler 2, after which the user may be alerted (thus possibly avoiding an exacerbation event) and/or whereby the user may be offered further training in use of the inhaler 2. A further advantage associated with use of the compliance monitor 1 is that the first portion 7 and second portion 8 are a push fit with respect to each other.

Hence, attaching the first portion 7 and second portion 8 together does not require any screwing action, as is the case for the compliance monitor described in NZ 614928—which can sometimes inadvertently rotate the rotatable base of the inhaler at the same time. Furthermore, being able to push the first portion 7 and second portion 8 together is a much simpler and quicker operation, as compared to having to screw the two portions 7 and 8 together. Moreover, the compliance monitors of the present invention do not require that any structural changes be made to the DPI itself, thereby ensuring that the function and efficacy of the DPI are not affected.

Whilst the preferred embodiments have been described in relation to a TURBUHALER® dry powder inhaler, it is envisaged that a corresponding embodiment could be used with a TWISTHALER® device or any other similar devices. Furthermore, it is also envisaged that the compliance of the 1 could be adapted for use with other dry powder medicament delivery devices, such as those used for the treatment of pain, heart conditions, erectile dysfunction, diabetes, and so on.

Variations

While the embodiments described above are currently preferred, it will be appreciated that a wide range of other variations might also be made within the general spirit and scope of the invention and/or as defined by the appended claims.

I claim:

1. A compliance monitor for monitoring patient usage of a dry powder medicament delivery device that includes:
   a) a store of medicament housed within a main body portion,
   b) a base portion, the base portion including a grip element and the base portion and the main body portion being rotatable with respect to each other through the rotation of the grip element,
   c) a medicament dispenser for dispensing a dose of the medicament into an inhalation chamber,
   d) a mouthpiece through which the dose of medicament may be inhaled by a user,
   e) a removable and replaceable cap,
   the compliance monitor comprising:
   f) a first portion for receiving the base portion of the medicament delivery device,
   g) a second portion configured to engage with the first portion to releasably secure the medicament delivery device to the first portion, thereby releasably attaching the compliance monitor to the medicament delivery device, and
   the arrangement and construction of the first and second portions being such that: the engaging of the second portion of the compliance monitor to the first portion of the compliance monitor includes a push fit and disengagement of the second portion from the first portion includes activation of a release; and
   the first portion and the second portion are configured to be releasably attachable to the medicament delivery device allowing repeated attachment to and removal from the medicament delivery device without requiring any physical modifications to the medicament delivery device.

2. A compliance monitor as claimed in claim 1, wherein the compliance monitor includes a dose detection sensor for determining if a dose of medicament has been dispensed and/or if the base portion has been rotated with respect to the main body portion.

3. A compliance monitor as claimed in claim 2, wherein the dose detection sensor can determine if the user only rotates the base portion once, and in one direction, with respect to the main body portion, and/or vice versa.

4. A compliance monitor, as claimed in claim 2, wherein the dose detection sensor includes:
   a) a rotor which holds the base of the dry powder medicament delivery device, the rotor being capable of rotating both ways in relation to the first portion of the compliance monitor,
   b) a torque sensor or torque switch comprising at least one leaf spring, wherein the torque sensor controls the rotation of the rotor,
   c) a switch engaged or disengaged by the movement of the rotor or the movement of the at least one leaf spring.

5. A compliance monitor as claimed in claim 1, wherein the compliance monitor includes a cap detection sensor for determining if the cap is attached to the medicament delivery device or is removed from the medicament delivery device.

6. A compliance monitor as claimed in claim 5, wherein the dose detection sensor and the cap detection sensor enable it to be determined if the user dispenses, or attempts to dispense, the dose of medicament when the cap is covering the mouthpiece of the medicament inhaler.

7. A compliance monitor, as claimed in claim 1, wherein the compliance monitor includes a device detection sensor for detecting if the compliance monitor is attached to, and/or removed from, the medicament delivery device.

8. A compliance monitor as claimed in claim 7, wherein the device detection sensor detects the presence of the medicament delivery device when the second portion of the compliance monitor is attached to the first portion of the compliance monitor.

9. A compliance monitor as claimed in claim 7, wherein the device detection sensor detects the removal of the medicament delivery device from the compliance monitor when the second portion of the compliance monitor is removed from the first portion of the compliance monitor.

10. A compliance monitor as claimed in claim 1, wherein the second portion of the compliance monitor is adapted to clip onto, or into, the first portion of the compliance monitor.

11. A compliance monitor as claimed in claim 1, wherein the release is a quick release, and wherein the first portion of the compliance monitor includes the quick release to release the second portion of the compliance monitor from the first portion of the compliance monitor.

12. A compliance monitor as claimed in claim 11, wherein the quick release includes at least one quick release button.

13. A compliance monitor as claimed in claim 1, wherein the release is a quick release, and wherein the second portion of the compliance monitor includes the quick release to release the first portion of the compliance monitor from the second portion of the compliance monitor.

14. A compliance monitor as claimed in claim 1, wherein an interior surface of the cap is provided with a first threaded portion, and an outside portion of the main body portion is provided with a complimentary second threaded portion, whereby the cap may be removed and attached, with respect to the medicament delivery device, by unthreading and threading, respectively, the first and second threaded portions with respect to each other; and wherein the action of screwing the cap to the main body portion has the effect of moving the medicament delivery device including the base portion within the second portion of the compliance monitor, and in a direction away from the first portion of the compliance monitor, and it is this action which causes the cap to be detected by the cap detection sensor as being attached and/or the action of unscrewing the cap from the main body portion has the effect of moving the medicament delivery device including the base portion within the second portion of the compliance monitor, and in a direction towards the first portion of the compliance monitor, and it is this action which causes the cap to be detected by the cap detection sensor as having been removed.

15. A compliance monitor as claimed in claim 1, wherein the compliance monitor is only operable, or in operation, when the second portion of the compliance monitor has been attached to the first portion of the compliance monitor.

16. A compliance monitor as claimed in claim 1, wherein the compliance monitor further includes an electronics control module (ECM), the ECM being adapted to monitor and/or manipulate and/or store and/or transmit all compliance data gathered, relating to the patient usage of the medicament delivery device.

17. A compliance monitor as claimed in claim 16, wherein the ECM utilises the compliance data gathered to determine if the user has used the medicament delivery device correctly and/or incorrectly.

18. A compliance monitor as claimed in claim 17, wherein the compliance monitor further includes an indicator to indicate an event and/or to alert the user if the ECM determines that the user has used the medicament delivery device correctly and/or incorrectly.

19. A compliance monitor as claimed in claim 18, wherein the indicator is in the form of a visual and/or audio and/or vibrational indicator.

20. A compliance monitor as claimed in claim 1, wherein the medicament delivery device is a dry powder inhaler.

21. A compliance monitor for monitoring patient usage of a dry powder medicament delivery device that includes:
    a) a store of medicament housed within a main body portion,
    b) a base portion, the base portion including a grip element and the base portion and the main body portion being rotatable with respect to each other through the rotation of the grip element,
    c) a medicament dispenser for dispensing a dose of the medicament into an inhalation chamber,
    d) a mouthpiece through which the dose of medicament may be inhaled by a user,
    e) a removable and replaceable cap,
    the compliance monitor comprising:
    f) a first portion for receiving the base portion of the medicament delivery device,
    g) a second portion configured to engage with the first portion to releasably secure the medicament delivery device to the first portion, thereby releasably attaching the compliance monitor to the medicament delivery device, and
    the arrangement and construction of the first and second portions being such that: the engaging of the second portion of the compliance monitor to the first portion of the compliance monitor does not include a screw fit and disengagement of the second portion from the first portion includes activation of a release; and
    the first portion and the second portion are configured to be releasably attachable to the medicament delivery device allowing repeated attachment to and removal from the medicament delivery device without requiring any physical modifications to the medicament delivery device.

* * * * *